United States Patent [19]

Fujiwara et al.

[11] Patent Number: 4,515,941

[45] Date of Patent: May 7, 1985

[54] 23-DEMYCINOSYLDESMYCOSIN DERIVATIVES

[75] Inventors: Tatsuro Fujiwara; Hideyuki Watanabe; Takao Hirano; Hideo Sakakibara, all of Shizuoka, Japan

[73] Assignee: Toyo Jozo Kabushiki Kaisha, Shizuoka, Japan

[21] Appl. No.: 480,398

[22] Filed: Mar. 30, 1983

[30] Foreign Application Priority Data

Apr. 7, 1982 [JP] Japan .................................. 57-58767
Nov. 27, 1982 [JP] Japan .............................. 57-207950
Dec. 28, 1982 [JP] Japan .............................. 57-227555

[51] Int. Cl.³ .......................................... C07H 17/08
[52] U.S. Cl. .................................... 536/7.1; 536/7.2
[58] Field of Search ........................ 536/7.1, 7.2, 118

[56] References Cited

U.S. PATENT DOCUMENTS 4,124,756 11/1978 Martin et al. ...................... 536/17 R
4,187,297 2/1980 Martin et al. ...................... 536/17 R
4,276,413 6/1981 Martin et al. ...................... 536/17 B

FOREIGN PATENT DOCUMENTS 5000 1/1982 Japan .................................... 536/7.1
2081711 2/1982 United Kingdom ................. 536/7.1

OTHER PUBLICATIONS

Richter, "Textbook of Organic Chemistry", 1938, John Wiley & Sons, Inc., New York, N.Y.

Primary Examiner—Johnnie R. Brown
Assistant Examiner—Elli Peselev
Attorney, Agent, or Firm—Ladas & Parry

[57] ABSTRACT

Novel 23-demycinosyldesmycosin derivatives are disclosed of the formula

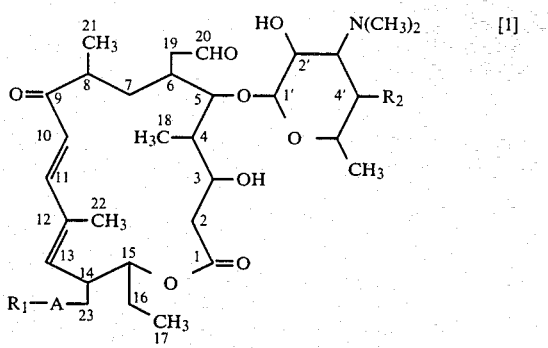

wherein A is oxygen or sulfur, $R_1$ is optionally substituted phenyl or

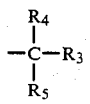

group, in which $R_3$ is optionally substituted phenyl and $R_4$ and $R_5$ are the same or different and are hydrogen, lower alkyl or optionally substituted phenyl, and $R_2$ is hydrogen or hydroxyl. The compounds or non-toxic salts thereof are useful as antibiotics.

5 Claims, No Drawings

23-DEMYCINOSYLDESMYCOSIN DERIVATIVES

This invention relates to a novel 23-demycinosyldesmycosin derivatives and process for producing the same. More particularly the present invention pertains to compounds of the formula

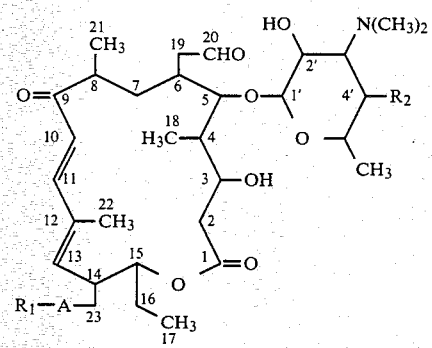
[1]

wherein A is oxygen or sulfur, $R_1$ is optionally substituted phenyl or

group, in which $R_3$ is optionally substituted phenyl and $R_4$ and $R_5$ are the same or different and are hydrogen, lower alkyl or optionally substituted phenyl, and $R_2$ is hydrogen or hydroxyl, or non-toxic salt thereof.

The present invention includes a process for production of a compound [1], or a non-toxic salt thereof, which comprises (A) O-alkylating a compound of the formula

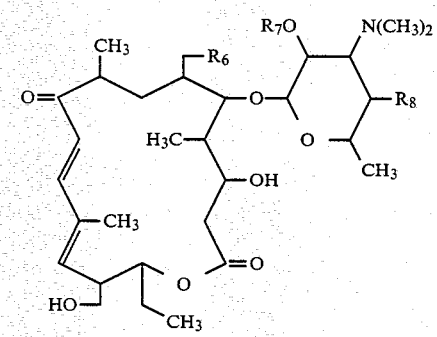
(3)

wherein $R_6$ is —CHO or

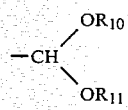

group, in which $R_{10}$ and $R_{11}$ are lower alkyl and $R_8$ is hydrogen or —$OR_7$ group, in which $R_7$ is protective group for hydroxyl, with an alkylating agent of the formula

wherein $R_3$ is optionally substituted phenyl, $R_4$ and $R_5$ are the same or different and are hydrogen, lower alkyl or optionally substituted phenyl and Y is halogen, in the presence of base;

(B) sulfonylating the hydroxyl at position-23 of the compound [3] hereinabove (A) with sulfonylhalide of the formula $R_9SO_2X$ wherein $R_9$ is phenyl, tolyl, nitrophenyl or bromophenyl and X is halogen, and O-arylating the thus obtained sulfonyl compound of the formula

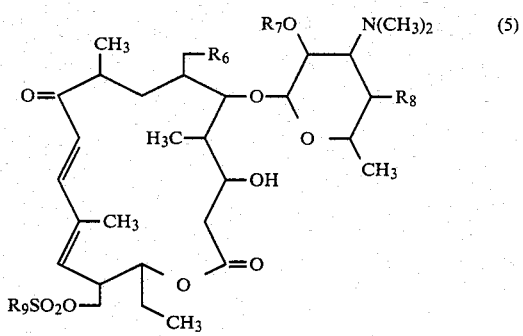
(5)

wherein $R_6$, $R_7$, $R_8$ and $R_9$ have the same meanings hereinbefore, with phenol of the formula $R_3$—OH wherein $R_3$ is optionally substituted phenyl, in the presence of etherification accelerator;

(C) 23-acetylthiolating the compound [5] hereinabove with alkaline metal thiol acetate and reacting the thus obtained acetylthio compound with alkylating agent of the formula

wherein $R_3$, $R_4$ and $R_5$ have the same meanings hereinbefore; or (D) reacting the compound [5] hereinbefore with thiol of the formula $R_3$—SH wherein $R_3$ has the same meaning hereinbefore, in the presence of etherification accelerator to obtain the compound of the formula

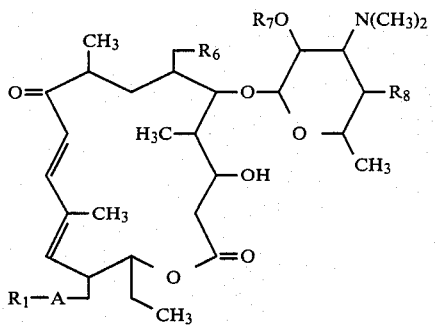

wherein A is oxygen or sulfur and $R_1$, $R_6$, $R_7$ and $R_8$ have the same meanings hereinbefore, and removing the protective group for hydroxyl, and in case of $R_6$ being

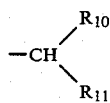

group, wherein $R_{10}$ and $R_{11}$ have the same meanings hereinbefore, de-acetylating the said compound.

Examples of pharmaceutically acceptable salts are salts of inorganic acids such as hydrochlorides, sulfates or phosphates and salts of organic acids such as acetates, propionates, tartrates, citrates, succinates, malates, aspartates or glutamates. Other non-toxic salts can be used.

The novel compound [1] has a stronger antibacterial activity against Gram positive bacteria as compared with known macrolide antibiotics such as erythromycin and tylosin, and also has an equivalent level of antibacterial activity against Gram negative bacteria as compared with that of erythromycin, and hence may be useful for clincal use. The antibiotic also is useful for feed additives and growth stimulants.

The starting material [3] of the present invention is a compound of the formula

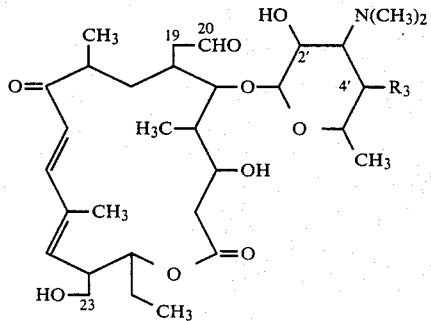

wherein $R_8$ is hydrogen or hydroxyl, in which, in the case that $R_8$ is hydroxyl, the hydroxyl at position-2' and -4' of 23-demycinosyldesmycosin [Tetrahedron Letters, 4737 (1970)] is protected, and in which in the case that $R_8$ is hydrogen, the hydroxyl at position-2' of 23-demycinosyl-4'-deoxydesmycosin [J. Antibiotics, 34(10), 1374–1376 (1981), Japan. Pat. Unexam. Publ. No. 57-28100] is protected, namely, 2',4'-di-O-acyl-23-demycinosyldesmycosin and 2'-O-acyl-23-demycinosyl-4'-deoxydesmycosin, or an acetal derivative thereof wherein aldehyde of the acyl derivative of these compounds is protected by acetalation.

Examples of protective groups are lower alkanoyls such as acetyl, propionyl or butyryl and halogenated acetyls such as chloroacetyl, dichloroacetyl, trichloroacetyl or trifluoroacetyl. Acetyl is preferred.

Introduction of the acetyl can be effected by reacting 23-demycinosyldesmycosin derivative [2] with acetic anhydride in an inert organic solvent. Preferred examples of inert organic solvents are dichloromethane, chloroform, dichloroethane or acetone. The reaction proceeds at room temperature, and can be checked by silica gel thin layer chromatography (TLC) or high performance liquid chromatography (HPLC), and can be stopped upon observing the disappearance of the compound [2].

The reaction product acyl derivative of the formula

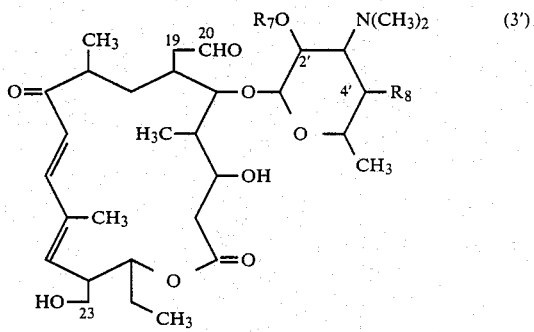

(compound [3] wherein $R_6$ is —CHO) can be isolated from the reaction mixture by adding water to the reaction mixture and extracting with a water-immiscible organic solvent such as chloroform, dichloroethane, methyl isobutyl ketone, ethyl acetate or butyl acetate at an alkaline pH 8–9.5. Further purification can be effected by column chromatography using silica gel, active alumina or an adsorption resin with an appropriate solvent such as benzene-acetone or chloroform-methanol.

Acetalation can be performed by conventional acetalation reaction for acyl derivative [3'], for example reacting with lower alcohol succh as methanol or ethanol in the presence of acid such as trifluoroacetic acid, trichloroacetic acid or p-toluenesulfonic acid. Isolation of the obtained acetal derivative, the compound [3], wherein $R_6$ is

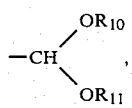

from reaction mixture can be performed by the same way as isolation of the above acyl derivative [3], and further purification can also be made by the same procedure.

The above protection of aldehyde by acetalation can also be made after obtaining acetylthio compound [10] wherein $R_6$ is —CHO hereinbelow. The acetalation reaction can be performed by the same procedure.

O-alkylation of the hydroxyl at position-23 in the starting substance [3] can be performed by reacting substance [3] with alkylating reagent 7 in the presence of base.

Examples of the above alkylating reagent [7'] are benzyl halide, β-phenylethylhalide, diphenylmethyl halide, tripheylmethyl halide, α-lower alkyl-phenylmethyl halide, α-di-loweralkyl-phenylmethyl halide or α-lower alkyl diphenylmethyl halide. Example of the above lower alkyl is an alkyl of $C_{1-4}$, such as methyl, ethyl, propyl, isopropyl, butyl, sec-butyl or t-butyl. The above phenyl is optionally substituted, for example by 1-3 substituents such as lower alkyl, lower alkoxyl or halogen. Example of halide is bromide or chloride.

Examples of base are an inorganic base such as sodium hydroxide, potassium hydroxide, sodium carbonate and potassium carbonate, and an organic base such as triethylamine or 4-dimethylaminopyridine.

O-alkylation can be performed in homogeneous solvent or two-phase solvents. Example of homogeneous solvent is nonpolar solvent such as benzene, toluene, dichloromethane, chloroform or dichloroethane. Example of two-phase solvents is a combination of benzene series solvent such as benzene or toluene and aqueous alkali such as sodium hydroxide or potassium hydroxide.

In the above reactions, the reaction in homogeneous solvent proceeds under heating, and the reaction in two phase solvents can be proceeded at room temperature. In the latter case, phase transfer catalyst such as tetrabutyl ammonium halide proceeds the reaction. The above etherification reaction can be traced by TLC or HPLC, and the reaction can be stopped upon observing disappearance of the starting material [3].

O-arylation of hydroxyl group at position-23 in the starting substance [3] can be proceeded by, at first, sulfonylating the hydroxyl group at position-23 in the compound [3], and, the second, subjected to react with phenol [6].

Sulfonylation of hydroxyl group at position-23 in the compound [3] can be made by reacting the compound [3] with sulfonyl halide [4] in an organic solvent in the presence of base. Examples of sulfonyl halide [4] are benzenesulfonyl halide, toluenesulfonyl halide such as p-toluenesulfonyl chloride or p-toluenesulfonyl bromide, nitrobenzenesulfonyl halide such as p-nitrobenzenesulfonyl chloride or p-nitrobenzenesulfonyl bromide, and bromobenzenesulfonyl halide such as p-bromobenzenesulfonyl bromide. Example of base is known tertiary organic amine. Examples of organic solvents are dichloromethane, chloroform, dichloroethane, benzene, tetrahydrofuran and dioxane, and pyridine can be used as base. Sulfonylation can be proceeded at room temperature and is stopped upon observing disappearance of the compound [3] by TLC or HPLC. Isolation and purification of the sulfonyl compound [5] can be made by the same procedure as of isolation and purification of acyl derivative [3'] hereinbefore.

In order to obtain the compound [9] by introducing 23-O-aryl group in sulfonyl compound [5], phenol [6] is reacted with sulfonyl compound [5] in the presence of etherification accelerator.

Examples of the above phenol [6] are optionally substituted phenol, preferably the formula of

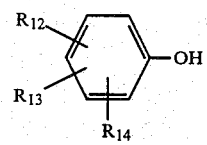

wherein $R_3$, $R_4$ and $R_5$ are the same or different, and are hydrogen, lower alkyl, lower alkoxy, halogen, nitro or di-lower alkylamino, for example phenol, p-(m- or o-) cresol, 2,3-(2,4-, 2,5-, 2,6-, 3,4- or 3,5-) xylenol, p-(m- or o-) ethylphenol, p-(m- or o-) methoxyphenol, p-(m- or o-) chlorophenol, p-(m- or o-) bromophenol, 2,3-(2,4-, 2,5-, 2,6-, 3,4- or 3,5-) dichlorophenol, p-(m- or o-) nitrophenol, p-(m- or o-) dimethylaminophenol, p-(m- or o-) diethylaminophenol or 2,6-di-t-butyl-4-cresol.

Examples of etherification accelerator are known alkylating agent for alcohol and phenol, for example fluoride-alumina such as LiF-alumina, NaF-alumina, KF-alumina, CsF-alumina or $Bu_4NF$-alumina. [Bull. Chem. Soc. Japan, 55, 2504–2507 (1982)].

O-arylation can be proceeded in organic solvent such as dimethylformamide, acetonitrile, dimethoxyethane or tetrahydrofuran. Reaction can be proceeded at room temperature and can be checked by TLC or HPLC and is stopped upon observing disappearance of sulfonyl compound [5]. Isolation and purification of the compound [9] can be made by the same way as that of the acyl derivative [3'] hereinbefore.

Thioetherification at position-23 of the starting substance [3] is performed as follows. The starting material [3] is converted to the above sulfonyl compound [5], which is 23-acetylthiolated by alkaline metal thioacetate to obtain the compound of the formula

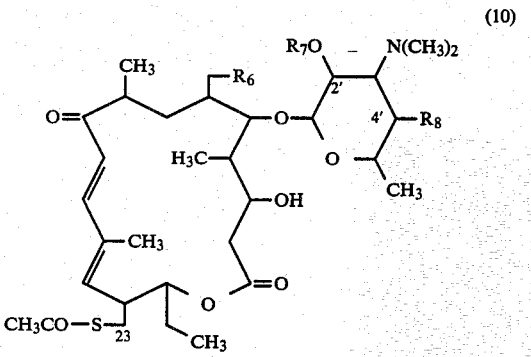

wherein $R_6$, $R_7$ and $R_8$ have the same meanings hereinbefore, and the said compound [10] is reacted with alkylating agent [7']. Or the sulfonyl compound [5] is reacted with thiol [8].

Reaction of the above sulfonyl compound [5] with alkaline metal thioacetic acid is performed in an organic solvent under heating. Example of alkaline metal thioacetic acid is potassium or sodium salt of thioacetic acid. Examples of organic solvent are dimethylformamide, dimethylacetamide, dimethylsulfoxide, tetrahydrofuran or dioxane. Reaction temperature is a boiling point of the above organic solvent or below, and preferably proceed at 60°–110° C. Reaction process can be checked by TLC or HPLC and is stopped upon observing disappearance of sulfonyl compound [5]. Isolation and purification of acethylthio compound [10] can be made by the same way as that of acyl derivatives [3'].

23-substituted thiolation of acetylthio compound [10] by alkylating agent [7] can be proceeded in the conventional organic solvent. Examples of alkylating agent are shown hereinbefore. Example of organic solvent is acetone or benzene. Examples of base are alkaline hydroxide such as potassium hydroxide, sodium hydroxide or alkaline carbonate such as potassium carbonate or sodium carbonate.

In the above reaction, advantageous result is obtained when adding crown ether as metal cation acceptor. Reaction process can be checked by TLC or HPLC and is stopped upon observing disappearance of acetylthio compound [10]. Reaction products [9] can be isolated and purified by the same way as the case of acyl derivative [3'] hereinbefore. Also 23-substituted thiol compound [9] can be obtained by reacting sulfonyl compound [5] with thiol [8].

Examples of thiol [8] are thiophenol and substituted thiophenol wherein benzene ring is substituted by, for example, 1-3 lower alkyl, lower alkoxy or halogen.

The above reaction is carred out in common organic solvent in the presence of base. Examples of organic solvents are acetonitrile, acetone or aqueous acetone. Examples of base are alkaline hydrogen carbonate such as sodium hydrogen carbonate or potassium hydrogen carbonate, and alkaline carbonate such as sodium carbonate or potassium carbonate. Reaction proceeds at room temperature or under heating. Reaction process can be checked by TLC or HPLC, and is stopped upon observing disappearance of sulfonyl compound [5]. Isolation of the product [9] can be made by the same way as before.

Removal of protective group for hydroxyl group at position-2' and -4' or position-2' in the reaction product [9] can be made by heating in lower alcohol optionally containing water. Examples of lower alcohol are methanol and ethanol and methanol is preferable. The above reaction can be checked by TLC or HPLC and is stopped upon observing disappearance of the compound [9].

Isolation of the reaction product can be performed by distilling off lower alcohol and extracting under alkaline pH of 8–9.5 with water immiscible organic solvent such as chloroform, dichloromethane, dichloroethane, methylisobutyl ketone, ethyl acetate or butyl acetate.

The above reaction product wherein if the aldehyde group is protected by acetal, can be deacetalated by hydrolyzing with acidic water. Reaction product can be isolated by the same way as hereinabove explained.

Removal of acetal may optionally be carried out before the process of removing protective group for hydroxyl.

The thus obtained product [1] can be purified by column chromatography using silica-gel, active alumina or adsorption-resin.

Minimum inhibitory concentrations(MIC) of the compound of the present invention are shown in the table 1.

Following referential example and examples illustrate the present invention. Rf values in the examples are, if not specified, measured by the TLC of the following carrier and developers.

Carrier: Merck DC-Fertig platten Kiesel gel 60F$_{254}$, *Art* 5715.

Developer:
a: benzene-acetone (3:1)
b: benzene-acetone (5:1)
c: chloroform-methanol-conc. ammonia (150:10:1)
d: chloroform-methanol-conc. ammonia (100:10:1)

REFERENTIAL EXAMPLE

2',4'-di-O-acetyl-23-demycinosyldesmycosin:

Acetic anhydride (16.73 ml, 5 molar excess) was added to 23-demycinosyldesmycosin (21.21 g, 35.5 mM) dissolved in dichloromethane (106 ml) and stirred at room temperature for 1.5 hour.

TABLE 1

MIC (mcg/ml)

compound −A−R₁

| test organisms | −O−C₆H₅ R₂=OH | | −O−C₆H₄−CH₃ (p) | | | −O−C₆H₄−C₂H₅ (p) OH | −O−C₆H₄−Cl (p) OH | −O−C₆H₄−Br (p) OH | −O−C₆H₃(Cl)₂ (2,4) OH | −O−C₆H₄−OCH₃ (p) OH | −O−C₆H₄−NO₂ (m) OH |
|---|---|---|---|---|---|---|---|---|---|---|---|
| | OH | EM | OH | TS | | | | | | | |
| Staphylococcus aureus ATCC 6538P | ≦0.05 | 0.2 | 0.4 | 0.4 | 0.8 | 0.1 | 0.2 | 0.1 | 0.2 | 0.2 | 0.1 |
| Staphylococcus aureus MS353 | ≦0.05 | 0.2 | 0.4 | 0.4 | 0.8 | 0.1 | 0.2 | 0.2 | 0.2 | 0.2 | 0.1 |
| Staphylococcus aureus MS353 C36 | ≦0.05 | 0.2 | 0.4 | 0.4 | 0.4 | ≦0.05 | 0.1 | 0.2 | 0.1 | 0.1 | 0.1 |
| Staphylococcus aureus MS353 A0* | 50 | 50 | 25 | 25 | >100 | 25 | 25 | 25 | 12.5 | 100 | 100 |
| Staphylococcus aureus 0119* | 100 | 50 | 25 | 25 | >100 | 50 | 25 | 25 | 25 | >100 | >100 |
| Staphylococcus aureus 0127* | 100 | 50 | 25 | 25 | >100 | 25 | 25 | 25 | 12.5 | >100 | >100 |
| Staphylococcus epidermis sp-al-1 | ≦0.05 | ≦0.05 | 0.2 | 0.1 | 0.2 | ≦0.05 | 0.1 | 0.1 | ≦0.05 | ≦0.05 | ≦0.05 |
| Streptococcus pyogenes N.Y.5 | ≦0.05 | ≦0.05 | 0.1 | 0.1 | >100 | ≦0.05 | ≦0.05 | ≦0.05 | ≦0.05 | >100 | >100 |
| Streptococcus pyogenes 1022* | 50 | 25 | 12.5 | 12.5 | >100 | 12.5 | 12.5 | 12.5 | 6.3 | 100 | 50 |
| Streptococcus faecalis 1501 | ≦0.05 | ≦0.05 | 0.4 | 0.1 | 0.4 | 0.1 | 0.2 | 0.2 | ≦0.05 | 0.2 | 0.1 |
| Streptococcus agalactiae 1020 | ≦0.05 | ≦0.05 | 0.1 | ≦0.05 | 0.1 | ≦0.05 | ≦0.05 | ≦0.05 | ≦0.05 | ≦0.05 | ≦0.05 |
| Sarcina lutea ATCC 9341 | ≦0.05 | ≦0.05 | ≦0.05 | ≦0.05 | >100 | ≦0.05 | ≦0.05 | ≦0.05 | ≦0.05 | ≦0.05 | ≦0.05 |
| Micrococcus flavus ATCC 10240 | ≦0.05 | ≦0.05 | ≦0.05 | ≦0.05 | >100 | ≦0.05 | ≦0.05 | ≦0.05 | ≦0.05 | ≦0.05 | ≦0.05 |
| Corynebacterium diptheriae P.Y.8 | ≦0.05 | ≦0.05 | ≦0.05 | ≦0.05 | >100 | ≦0.05 | ≦0.05 | ≦0.05 | ≦0.05 | ≦0.05 | ≦0.05 |
| Bacillus subtilis ATC 6633 | ≦0.05 | 0.1 | 0.4 | 0.4 | >100 | 0.1 | 0.2 | 0.2 | 0.1 | 0.2 | 0.1 |
| Escherichia coli NIHJ-JC2 | 50 | 100 | >100 | >100 | >100 | 50 | 50 | 50 | >100 | 100 | 100 |
| Escherichia coli B | 25 | 50 | >100 | >100 | >100 | 50 | 25 | 25 | >100 | 50 | 50 |
| Klebsiella pneumoniae ATCC 10031 | 1.6 | 6.3 | >100 | >100 | >100 | 3.1 | 3.1 | 3.1 | 3.1 | 3.1 | 1.6 |
| Salmonella typhosa H901 | 100 | >100 | >100 | >100 | >100 | >100 | >100 | >100 | >100 | >100 | 100 |
| Salmonella enteritidis Gaertner | 100 | >100 | >100 | >100 | >100 | >100 | >100 | >100 | >100 | >100 | >100 |
| Shigella flexineri type 3a | 6.3 | 50 | >100 | >100 | >100 | 6.3 | 12.5 | 12.5 | 25 | 50 | 12.5 |
| Shigella sonnei E33 | 50 | >100 | >100 | >100 | >100 | 50 | 100 | 100 | 100 | >100 | 100 |
| Proteus vulgaris OX19 | 12.5 | 25 | 100 | 100 | >100 | 12.5 | 25 | 25 | 25 | 50 | 25 |
| Serratia marcescens | 50 | 100 | >100 | >100 | >100 | 50 | 50 | 50 | 25 | >100 | 50 |
| Pseudomonas aeruginosa IAM 1095 | 50 | >100 | >100 | >100 | >100 | >100 | >100 | >100 | >100 | >100 | 50 | compound −A−R₁

| test organisms | −O−C₆H₄−N(C₂H₅)₂ (m) R₂=OH | −S−CH₂C₆H₅ OH | −S−(CH₂)₂C₆H₅ OH | −S−CH(CH₃)C₆H₅ OH | −S−C₆H₅ OH | −O−CH₂C₆H₅ OH | −O−C(C₆H₅)₃ OH | | |
|---|---|---|---|---|---|---|---|---|---|
| | | | | | | | | EM | TS |
| Staphylococcus aureus ATCC 6538P | 0.8 | ≦0.05 | 0.1 | 0.2 | 0.1 | ≦0.05 | 1.6 | 0.1 | 0.8 |
| Staphylococcus aureus MS353 | 0.4 | ≦0.05 | 0.1 | 0.2 | 0.1 | ≦0.05 | 1.6 | 0.1 | 0.8 |
| Staphylococcus aureus MS353 C36 | 0.4 | | | | | | | | |
| Staphylococcus aureus MS353 A0* | 25 | 50 | 50 | 25 | 25 | 50 | 6.3 | >100 | >100 |
| Staphylococcus aureus 0119* | 50 | | | | | | | | |
| Staphylococcus aureus 0127* | 25 | — | — | — | — | 100 | 25 | — | — |
| Staphylococcus epidermis sp-al-1 | 0.2 | ≦0.05 | ≦0.05 | ≦0.05 | ≦0.05 | ≦0.05 | 1.6 | 1.1 | 0.4 |
| Streptococcus pyogenes N.Y.5 | 0.1 | ≦0.05 | ≦0.05 | ≦0.05 | ≦0.05 | ≦0.05 | 0.8 | ≦0.05 | 0.1 |
| Streptococcus pyogenes 1022* | 12.5 | — | 25 | 25 | 25 | 3.1 | 3.1 | >100 | 25 |

TABLE 1-continued

MIC (mcg/ml)

| Organism | | | | | | | | |
|---|---|---|---|---|---|---|---|---|
| Streptococcus faecilis 1501 | 0.2 | 0.2 | ≦0.05 | 0.1 | 0.2 | ≦0.05 | 0.05 | 1.6 | 0.2 | 1.6 |
| Streptococcus agalactiae 1020 | 0.1 | ≦0.05 | ≦0.05 | ≦0.05 | 0.1 | ≦0.05 | ≦0.05 | 1.6 | ≦0.05 | 0.4 |
| Sarcina lutea ATCC 9341 | 0.1 | ≦0.05 | ≦0.05 | ≦0.05 | 0.05 | ≦0.05 | ≦0.05 | 0.4 | ≦0.05 | ≦0.05 |
| Micrococcus flavus ATCC 10240 | 0.1 | 0.1 | ≦0.05 | — | ≦0.05 | | | | | |
| Corynebacterium diptheriae P.Y.8 | ≦0.05 | ≦0.05 | ≦0.05 | 0.1 | ≦0.05 | ≦0.05 | ≦0.05 | 0.1 | ≦0.05 | ≦0.05 |
| Bacillus subtilis ATC 6633 | 0.2 | 0.2 | 0.1 | — | 0.2 | 0.1 | ≦0.05 | 3.1 | ≦0.05 | 0.2 |
| Escherichia coli NIHJ-JC2 | >100 | >100 | 50 | 0.2 | 50 | 50 | 25 | >100 | 100 | >100 |
| Escherichia coli B | >100 | >100 | | 50 | | | | | | |
| Klebsiella pneumoniae ATCC 10031 | 3.1 | 50 | 1.6 | 3.1 | 3.1 | 1.6 | 6.3 | >100 | 6.3 | 100 |
| Salmonella typhosa H901 | >100 | >100 | 50 | >100 | 100 | 50 | 100 | >100 | 50 | >100 |
| Salmonella eneteriidis Gaertner | >100 | >100 | | | | | | | | |
| Shigella flexineri type 3a | 12.5 | 50 | | | | | | | | |
| Shigella sonnei E33 | >100 | >100 | 25 | 25 | 50 | 50 | 25 | >100 | 100 | >100 |
| Proteus vulgaris OX19 | 25 | 50 | 6.3 | 12.5 | 12.5 | 12.5 | 3.1 | >100 | 25 | >100 |
| Serratia marcescens | >100 | >100 | | | | | | | | |
| Pseudomonas aeruginosa IAM 1095 | >100 | >100 | 100 | >100 | >100 | 100 | 50 | >100 | 100 | >100 |

\*macrolide resistant bacteria A group (clinical isolates of erythromycin, oleandomycin and 16-membered macrolide antibiotic resistant strains.)
EM: erythromycin
TS: tylosin Reaction mixture was poured into diluted aqueous ammonia (400 ml) and extracted with chloroform (300 ml). Aqueous layer was reextracted with chloroform (300 ml). Combined organic layer was dehydrated by anhydrous magnesium sulfate and dried up in vacuo to obtain 2',4'-di-O-acetyl-23-demycinosyldesmycosin (24.0 g. yield: 99.3%).

TLC: Rfc=0.13, Rfa=0.32

EXAMPLE 1

23-O-benzyl-23-demycinosyldesmycosin:

Benzene (5 ml) containing 50% sodium hydroxide (0.176 ml, 5 molar excess) was added to 2',4'-di-O-acetyl-23-demycinosyldesmycosin (300 mg, 0.4399 mM). Tetrabutylammonium bromide (7.1 mg, 0.05 equimolar) and followed by benzylbromide (0.262 ml, 5 molar excess) are added therein and vigorously stirred at room temperature for one hour. Reaction mixture was poured into water (20 ml) and shaked. Benzene layer was passed through Whatman 1 PS filter paper and concentrated in vacuo to obtain pale yellow oily material (0.44 g), which was purified by preparative silica-gel TLC (20×20 cm, 2 plates, Merck Art 5717) using benzene-acetone (3:1). Band showing Rfa=0.65 was scratched off and extracted with chloroform-methanol (3:1). Extract was concentrated in vacuo to obtain 2',4'-di-O-acetyl-23-O-benzyl-23-demycinosyldesmycosin (37 mg), which was dissolved in methanol (5 ml) and heated at 55° C. for 19 hours. Reaction mixture was concentrated in vacuo. Diluted aqueous ammonis was added to the residue and extracted with chloroform. Chloroform layer was passed through Whatman 1 PS and concentrated in vacuo to obtain foamy 23-O-benzyl-23-demycinosyldesmycosin (33 mg, yield: 10.9%).

TLC: Rfd=0.32

NMR (FX—100, CDCl$_3$) δppm; 1.81 (s., 3H, C$_{12}$—CH$_3$), 2.50 (s., 6H,

3.52 (d., 2H, 23—CH$_2^-$), 4.26 (d., 1H, H—1'), 4.50 (s. 2H, CH$_2$C$_6$H$_5$), 5.00 (d. t., 1H, H$_{15}$), 5.88 (d., 1.H, H$_{13}$), 6.27 (d., 1H, H$_{11}$), 7.32 (s., 5H, phenyl), 7.32 (d., 1H, H$_{11}$), 9.69 (s., 1H, CHO)

MS (CI isobutane); 688 (MH+), 670 (MH+—18), 192, 174, 108

EXAMPLE 2

23-O-triphenylmethyl-23-demycinosyldesmycosin:

Dry dichloromethane (10 ml) and 4-dimethylamino-1-triphenylmethyl pyridinium chloride [Tetrahedron Letters, 22(16), 1491-1494 (1981)] (235 mg, 2 molar excess) were added to 2',4'-di-O-acetyl-23-demycinosyldesmycosin (200 mg, 0.2934 mM) and refluxed for 16 hours. Aqueous ammonia was added to the reaction mixture for adjusting aqueous layer to pH 8-9, and extracted with chloroform. Chloroform layer was passed through Whatman 1 PS and concentrated in vacuo to obtain the product (0.55 g), which was purified by preparative silica-gel TLC (20×20 cm, 2 plates, Merck Art 5717) using benzene-acetone (3:1). Band showing Rfa=0.63 was collected was extracted with chloroform methanol (3:1). Extract was concentrated to obtain white foamy 2',4'-di-O-acetyl-23-O-triphenylmethyl-23-demycinosyldesmycosin (183 mg), which was dissolved in methanol (5 ml) and heated at 55° C. for 4 hours. Reaction product was concentrated in cacuo and diluted aqueous ammonia was added to the residue, then extracted with chloroform. Chloroform layer was passed through Whatman 1 PS and concentrated in vacuo to obtain white foamy 23-O-triphenylmethyl-23-demycinosyldesmycosin (154 mg, yield: 62.4%).

TLC: Rfd=0.36

NMR (FX—100, CDCl$_3$) δppm; 1.80 (s., 3H, C$_{12}$—CH$_3$), 2.50 (s., 6H,

4.27 (d., 1H, H—1'), 5.03 (d. t., 1H, H—15), 6.05 (d., 1H, H—13), 6.29 (d., 1H, H—10), 7.2~7.5 (m., 15H, 7I=N×3), 9.71 (s., 1H, CHO)

MS; 840 (MH+), 822, 243, 192, 174

EXAMPLE 3

2',4'-di-O-acetyl-23-demycinosyldesmycosin dimethylacetal:

Trifluoroacetic acid (3 ml) was added under ice-cooling to 2',4'-di-O-acetyl-23-demycinosyldesmycosin (4.23 g) dissolved in methanol (27 ml), and stirred at room temperature for 2 hours. Reaction mixture was poured into 7% aqueous ammonia and extracted with chloroform. Chloroform layer was washed with water, passed through Whatman 1 PS filter paper and concentrated in vacuo to obtain foamy 2',4'-di-O-acetyl-23-demyconosyldesmycosin dimethyl=acetal (3.96 g).

TLC: Rfa=0.35, Rfb=0.15

EXAMPLE 4

2',4'-di-O-acetyl-23-demycinosyl-23-O-(p-nitrobenzenesulfonyl)-desmycosin dimethylacetal:

Para-nitrobenzenesulfonyl chloride (910 mg, 1.5 equimolar) was added to 2',4'-di-O-acetyl-23-demycinosyldesmycosin dimethylacetal (2 g, 2.748 mM) dissolved in pyridine (10 ml) and stirred for 1 hour. Further p-nitrobenzenesulfonyl chloride (300 mg) was added and stirred for 1 hour. Reaction mixture was poured into cold 7% aqueous ammonia saturated with sodium chloride. Orange colored precipitate was filtered and dissolved in chloroform, which was washed with water, passed through Whatman 1 PS filter paper and concentrated in vacuo. Residue was charged on a column of silica-gel (25 g, Merck Art 7734) and eluted with benzene-acetone (5:1). Fractions showing Rfb=0.38 were collected and dried up in vacuo to obtain foamy 2',4'-di-O-acetyl-23-demycinosyl-23-O-(p-nitrobenzenesulfonyl)-desmycosin dimethylacetal (1.41 g).

EXAMPLE 5

23-O-(p-tolyl)-23-demycinosyldesmycosin:

KF-Al$_2$O$_3$ (900 mg, 10 molar excess) and p-cresol (314 μl, 5 molar excess) were added to 2',4'-di-O-acetyl-23-demycinosyl-23-O-(p-nitrobenzenesulfony)-desmycosin dimethylacetal (547.2 mg, 0.6 mM) dissolved in acetonitrile (5 ml) and stirred at room temperature for 1 day. Reaction mixture was filtered by suction and alumina on the filter paper was washed completely with diethyl ether, then the filtrate was concentrated in vacuo. Residue (753.3 mg) was charged on a column of silica-gel (Merck Art 7734, 30 g) and eluted with benzene-acetone (20:1-10:1). Fractions showing Rfa=0.55 were collected and concentrated invacuo to obtain 2',4'-di-O-acetyl-23-O-(p-tolyl)-23-demycinosyldesmycosin dimethylacetal (369.2 mg).

The product dissolved in methanol (5 ml) was heated at 55° C. for 6 hours to remove 2',4'-di-O-acetyl-group and the reaction mixture was concentrated in vacuo. Residue dissolved in 90% trifluoroacetic acid (2 ml) under ice-cooling was stirred for 15 minutes to romove dimethylacetal. Reaction mixture was poured into water, adjusting pH 8–9 by adding aqueous ammonia, then extracted three times with chloroform. Extract was dried by anhydrous magnesium sulfate and dried up in vacuo to obtain crude 23-O-(p-tolyl)-23-demycinosyldesmycosin (270.8 mg). The product was charged on a column of silica-gel (12 g, Merck Art 7734) and eluted with chloroform-methanol (100:1-10:1). Fractions showing Rfc=0.48 were collected and dried up in vacuo to obtain 23-O-(p-tolyl)-23-demycinosyldesmycosin (89.8 mg).

TLC; Rfc=0.48

NMR (FX—100, CDCl$_3$) δppm; 1.83 (s.,3H, C$_{12}$—CH$_3$), 2.28 (s., 3H,—C$_6$H$_4$—CH$_3$), 2.51 (s.,6H, (CH$_3$)$_2$N—), 4.01(d., 2H, H—23), 4.26 (d.,1H, H—1'), 5.16 (d.t., 1H, H—15), 5.94 (d., 1H, H—13), 6.29 (d., 1H, H—10), 6.77 (d., 2H, p-tolyl 2,6-proton), 7.08 (d.,2H, p-tolyl 3,5-proton), 7.33 (d., 1H, H—11), 9.70 (s.,1H,—CHO)

MS (CI); 688 (MH$^+$), 670 (MH$^+$—18), 192, 174

EXAMPLE 6

23-O-phenyl-23-demycinosyldesmycosin:

KF-Al$_2$O$_3$ (900 mg, 10 molar excess) and phenol (282 mg, 5 molar excess) were added to 2',4'-di-O-acetyl-23-demycinosyl-23-O-(p-nitrobenzenesulfonyl)-desmycosin dimethylacetal (547.2 mg, 0.6 mM) dissolved in acetonitrile (5 ml) and stirred at room temperature for 1 day. Reaction mixture was filtered by sucsion and alumina on the filter paper was washed well with diethyl ether, then filtrate was dried up in vacuo. Residue was charged on a column of silica-gel (30 g, Merck Art 7734) and eluted with benzene-acetone (20:1-10:1). Fractions showing Rfa=0.45 were collected and dried up in vacuo to obtain 2',4'-di-O-acetyl-23-O-phenyl-23-demycinosyldesmycosin dimethylacetal (337.1 mg), which was dissolved in methanol (5 ml). The solution was heated at 55° C. for 6 hours and concentrated in vacuo. Residue was dissolved in 90% trifluoroacetic acid (2 ml) under ice-cooling and stirred for 15 minutes. Reaction mixture was poured into water, adjusting pH of aqueous layer to pH 8–9 by adding aqueous ammonia, then extracted three times with chloroform. Chloroform layer was dried by anhydrous magnesium sulfate and dried up in vacuo. Residue was charged on a column of silica-gel (12 g, Merck Art 9385) and eluted by flush chromatography with chloroform-methanol (300:1-200:1). Fractions showing Rfc=0.44 were collected and dried up in vacuo to obtain 23-O-phenyl-23-demycinosyldesmycosin (162.8 mg, yield: 39.5%).

TLC; Rfc=0.44

NMR (FX—100, CDCl$_3$) δppm; 1.84 (s., 3H, 12—CH$_3$), 2.51 (s., (CH$_3$)$_2$ N—), 4.05 (d., H—23), 4.26 (d., H—1'), 5.16 (d.t., H—15), 5.94 (d., H—13), 6.29 (d., H—10), 6.8~7.1 (m., phenyl 3, 4, 5-proton), 7.2~7.4 (m., phenyl 2, 6-proton, H—11), 9.70 (s., CHO)

MS (CI): 674 (MH$^+$), 656, 192, 174.

EXAMPLE 7

23-O-(m-nitrophenyl)-23-demycinosyldesmycosin:

In example 5, p-cresol (314 μl) was replaced by m-nitrophenyl (418 mg) and reaction was carried out for 2 days to obtain 2',4'-di-O-acetyl-23-O-(m-nitrophenyl)-23-demycinosyldesmycosin dimethylacetal (426.9 mg). TLC: Rfa=0.47.

The product was treated according to the method in example 5 with removal of 2',4'-di-O-acetyl group, removing dimethylacetal and purification to obtain 23-O-(m-nitrophenyl)-23-demycinocyldesmycosin (263.9 mg, yield: 28.5%).

TLC; Rfc=0.47

NMR (FX—100, CDCl$_3$) δppm; 1.86 (s.), 2.55 (s.), 4.13 (d.), 4.27 (d.), 5.16 (d.t.), 5.94 (d.), 6.32 (d.), 7.27 (d.t., 1H, m-nitrophenyl 6-proton), 7.32 (d.), 7.46 (t., 1H, m-nitrophenyl 5-proton), 7.71 (m-nitrophenyl 2-proton), 7.86 (d.t.,1H, m-nitrophenyl 4-proton), 9.70 (s.)

MS (CI); 719 (MH$^+$), 702, 580 (MH$^+$-m-nitrophenol), 192, 174, 140 (m-nitrophenol+1)

EXAMPLE 8

23-O-(p-methoxyphenyl)-23-demycinosyldesmycosin:

In example 5, p-cresol (314 μl) was replaced by p-methoxyphenol (373 mg) to obtain 2',4'-di-O-acetyl-23-O-(p-methoxyphenyl)-23-demycinosyldesmycosin dimethylacetal (283.3 mg).

TLC: Rfa=0.46

The product was treated according to the method in example 5 with removing 2',4'-di-O-acetyl group and dimethylacetal to obtain crude 23-O-(p-methoxyphenyl)-23-demycinosyldesmycosin, which was purified by using preparative silica-gel TLC (Merck, Art 5717, 20×20 cm, 2 plates) eluting with chloroform-methanol-conc. aq. ammonia (150:10:1). Fractions showing Rfc=0.47 were scratched off and eluted with chloroform-methanol (1:1). Eluate was dried up in vacuo to obtain purified substance (77.8 mg).

TLC; Rfc=0.47

NMR (FX—100, CDCl$_3$) δppm; 1.83 (s.), 2.57 (s.), 3.77 (s., 3H, CH$_3$ O—C$_6$H$_4$—), 3.99 (d.), 4.27 (d.), 5.13 (d,t.), 5.95 (d.), 6.29 (d.), 6.82 (s., 4H, p-methoxyphenyl 2, 3, 5, 6-proton), 7.33 (d.), 9.69 (s.)

MS (CI); 704 (MH$^+$), 686 (MH$^+$—18), 192, 174, 125 (p-methoxyphenyl+1)

EXAMPLE 9

23-O-(p-chlorophenyl)-23-demycinosyldesmycosin:

In example 5, p-cresol (314 μl) was replaced by p-chlorophenol (387 mg) to obtain 2',4'-di-O-acetyl-23-O-(p-chlorophenyl)-23-demycinosyldesmycosin dimethylacetal (382.9 mg).

TLC: Rfa=0.55

The substance was dissolved in methanol (5 ml) and heated at 55° C. for 6 hours for removal of 2',4'-di-O-acetyl group, then concentrated in vacuo. Residue dissolved in 90% trifluoroacetic acid (2 ml) under ice-cooling was stirred for 15 minutes to remove dimethylacetal. Reaction mixture was poured into water, adjusting pH of the aqueous layer to pH 8–9 by aqueous ammonia and extracted three times with chlororform. Chloroform layer was dried by anhydrous magnesium sulfate and dried up in vacuo to obtain 23-O-(p-chlorophenyl)-23-demycinosyldesmycosin (298.8 mg, yield: 39.5%).

TLC; Rfc=0.48

NMR (FX—100, CDCl$_3$) δppm; 1.83 (s.), 2.50 (s.), 4.01 (d.), 4.26 (d.), 5.09 (d.t.), 5.92 (d.), 6.30 (d.), 6.81 (d., 2H, p-chlorophenyl 2, 6-proton), 7.24 (d., 2H, p-chlorophenyl 3, 5-proton), 7.31 (d.), 9.69 (s.)

MS (CI); 710, 708 (MH+), 692, 690 (MH+—18), 192, 174

EXAMPLE 10

23-O-(m-diethylaminophenyl)-23-demycinosyldesmycosin:

In example 5, p-cresol (314 μl) was replaced by m-diethylaminophenol (496 mg) to obtain 2',4'-di-O-acetyl-23-O-(m-diethylaminophenyl)-23-demycinosyldesmycosin dimethylacetal (354.7 mg).

TLC: Rfa=0.39

The said substance was treated, according to a method described in example 9, with removing 2',4'-di-O-acetyl group and dimethylacetal to obtain 23-O-(m-diethylaminophenyl)-23-demycinosyldesmycosin. Yield: 35.7%.

TLC; Rfc=0.51

NMR (FX—100, CDCl$_3$) δppm;1.84 (s.), 2.51 (s.), 3.33 (q., 4H, —N (CH$_2$CH$_3$)$_2$), 4.02 (d.), 4.27 (d.), 5.16 (d.t.), 5.98 (d.), 6.06~6.31 (m., 3H, phenyl 2,4,6-proton), 7.10 (t., 1H, phenyl 5-proton), 7.34 (d.), 9.69 (s.)

MS (CI); 745 (MH+), 727 (MH+—18), 192, 174

EXAMPLE 11

23-O-(p-ethylphenyl)-23-demycinosyldesmycosin:

In example 5, p-cresol (314 μl) was replaced by p-ethylphenol (367 mg) to obtain 2',4'-di-O-acetyl-23-O-(p-ethylphenyl)-23-demycinosyldesmycosin dimethylacetal (368.3 mg).

TLC: Rfa=0.49

The above compound was treated, according to a method of example 5, by removing 2',4'-di-O-acetyl group and dimethylacetal to obtain 23-O-(p-ethylphenyl)-23-demycinosyldesmycosin (217.2 mg).

TLC; Rfc=0.50

NMR (FX—100, CDCl$_3$) δppm; 1.2~1.3 (m., 3H, —CH$_2$CH$_3$), 1.84 (s.), 2.54 (s.), 2.4~2.6 (m., 2H, —CH$_2$CH$_3$), 4.02 (d.), 4.27 (d.), 5.16 (d.t.), 6.29 (d.), 6.80 (d., 2H, phenyl 2, 6-proton), 7.12 (d., 2H, phenyl 3, 5-proton), 7.32 (d.), 9.70 (s.)

MS (CI); 702 (MH+), 684 (MH+—18), 192, 174

EXAMPLE 12

23-O-(p-bromophenyl)-23-demycinosyldesmycosin:

In example 5, p-cresol (314 μl) was replaced by p-bromophenol (519 mg) to obtain 2',4'-di-O-acetyl-23-O-(p-bromophenyl)-23-demycinosyldesmycosin dimethylacetal (406.8 mg).

TLC: Rfa=0.40

The above product was treated, according to a method of example 9, by removing 2',4'-di-O-acetyl group and dimethylacetal to obtain 23-O-(p-bromophenyl)-23-demycinosyldesmycosin. Yield: 41.0%

TLC: Rfc=0.50

NMR (FX—100, CDCl$_3$) δppm; 1.84(s.), 2.51 (s.), 4.01(d.), 4.26(d.), 5.10(d.t.), 5.92(d.), 6.30(d.), 6.76(d.t., 2H, phenyl 2,6-proton), 7.32(d.), 7.38(d.t., 2H, phenyl 3.5-proton), 9.70(s.)

MS (CI): 754, 752 (MH+), 736, 734 (NH+—18), 192, 174

EXAMPLE 13

23-O-(2,4-dichlorophenyl)-23-demycinosyldesmycosin:

In example 5, p-cresol (314 μl) was replaced by 2,4-dichlorophenol (489 mg) to obtain 2',4'-di-O-acetyl-23-O-(2,4-dichlorophenyl)-23-demycinosyldesmycosin dimethylacetal (449.5 mg).

TLC: Rfa=0.43

The above product was purified, according to a method of example 5, by removing 2',4'-di-O-acetyl group and dimethylacetal to obtain 23-O-(2,4-dichlorophenyl)-23-demycinosyldesmycosin (293.6 mg, yield: 37.0%).

TLC: Rfc=0.51

NMR (FX—100, CDCl$_3$) δppm: 1.86(s.), 2.51(s.), 4.07(d.), 4.26(d.), 5.16(d.t.), 5.92(d.), 6.30(d.), 6.80(d., 1H, phenyl 6-proton), 7.18(d.d., 1H, phenyl 5-proton), 7.32(d.), 7.37(d., 1H, phenyl 3-proton), 9.70(s.)

MS (CI): 746, 744, 742 (MH+), 728, 726, 724 (MH+—18), 192, 174.

EXAMPLE 14

23-O-(2,6-di-t-butyl-4-tolyl)-23-demycinosyldesmycosin:

In example 5, p-cresol (314 μl) was replaced by 2.6-t-butyl-4-cresol (661 mg) to obtain 2',4'-di-O-acetyl-23-O-(2,6-di-t-butyl-4-tolyl)-23-demycinosyldesmycosin dimethylacetal (166.8 mg).

TLC: Rfa=0.48

The above product was treated, according to a method of example 5, by removing 2',4'-di-O-acetyl group and dimethylacetal to obtain crude 23-O-(2,6-di-t-butyl-4-tolyl)-23-demycinosyldesmycosin (123.6 mg), which was purified by silica-gel preparative TLC described in example 8 to obtain purified product (70.1 mg).

TLC; Rfc=0.56

NMR (FX—100, CDCl$_3$) δppm; 1.39 (s., 18H, t-butyl×2), 1.89 (s.), 2.27 (s., 3H, CH$_3$—C$_6$H$_4$—), 2.57 (s.), 4.28 (d.), 4.90 (d.t.), 5.88 (d.), 6.28 (d.), 7.03 (s.,2H, phenyl 3,5-proton), 7.34 (d.), 9.70(s.)

MS (CI); 800 (MH+), 782 (MH+—18), 220 (2,6-t-butyl-4-cresol), 192, 174

EXAMPLE 15

2',4'-di-O-acetyl-23-demycinosyl-23-O-tosyldesmycosin:

2',4'-di-O-acetyl-23-demycinosyldesmycosin (6.03 g, 8.35 mM) and p-toluenesulfonyl chloride (2.53 g, 1.5 equimolar) were dissolved in pyridine (3.0 ml) and stirred at room temperature for 5 hours. Reaction mixture was slowly dropped into water (600 ml) which was adjusted to pH 9–10 by 7% aqueous ammonia, stirred, and the supernatant solution was removed by decantation, then the residue was dissolved in chloroform (500 ml). Water (500 ml) was added to chloroform solution, adjusted to pH 2 by 1N HCl, washed, and further washed twice with water (50 ml), 7% aqueous ammonia and three times with water (300 ml), in this order. The solution was dried by anhydrous magnesium sulfate, and chloroform was distilled off in vacuo to obtain pale yellow foamy solid 2',4'-di-O-acetyl-23-demycinosyl-23-O-tosyldesmycosin (5.92 g).

TLC: Rfb=0.38

EXAMPLE 16

2',4'-di-O-acetyl-23-acetylthio-23-demycinosyl-23-deoxydesmycosin:

2',4'-di-O-acetyl-23-demycinosyl-23-O-tosyldesmycosin (2.585 g, 3.088 mM) and potassium thioacetate (422 mg, 1.2 equimolar) were dissolved in dimethylformamide (15 ml) and stirred at 70° C. for 80 minutes. Reaction mixture was poured into 7% aqueous ammonia saturated with sodium chloride and the precipitate was collected. The precipitate dissolved in chloroform was washed with 7% aqueous ammonia, passed through Whatman 1PS filter paper and concentrated in vacuo. Residue was charged on a column of silica-gel (Merck Art 7734) and eluted with chloroform. Fractions showing Rfa=0.41 were collected and dried up in vacuo to obtain foamy solid 2',4'-di-O-acetyl-23-acetylthio-23-demycinosyl-23-deoxydesmycosin (1.73 g).

EXAMPLE 17

2',4'-di-O-acetyl-23-demycinosyldesmycosin dimethylacetal:

Trifluoroacetic acid (3 ml) was added under ice-cooling to 2',4'-di-O-acetyl-23-demycinosyldesmycosin (4.23 g) dissolved in methanol (27 ml) and stirred at room temperature for 2 hours. Reaction mixture was poured into 7% aqueous ammonia and extracted with chloroform. Chloroform layer was washed with water, passed through Whatman 1PS filter paper and dried up in vacuo to obtain foamy solid 2',4'-di-O-acetyl-23-demycinosyldesmycosin dimethylacetal (3.96 g).

TLC; Rfa=0.35, Rfb=0.15

EXAMPLE 18

2',4'-di-O-acetyl-23-demycinosyl-23-O-tosyldesmycosin dimethylacetal:

2',4'-di-O-acetyl-23-demycinosyldesmycosin dimethylacetal (1.5 g) and p-toluenesulfonyl chloride (785 mg, 2.0 equimolar were dissolved in pyridine (7.5 ml) and stirred at room temperature for 5 hours. Reaction mixture was poured into cold 7% aqueous ammonia saturated with sodium chloride and the precipitated yellow porridge-like substance was collected by filtration, then dissolved in chloroform. The chloroform solution was washed with water, passed through Whatman 1PS filter paper and concentrated in vacuo. Residue was charged on a column of silica-gel (Merck Art 7734) and eluted with chloroform (600 ml) followed by chloroform-methanol (100:1). Fractions showing Rfb=0.38 were collected and dried up in vacuo to obtain foamy solid 2',4'-di-O-acetyl-23-demycinosyl-23-O-tosyldesmycosin dimethylacetal (1.32 g). TLC: Rfa=0.60, Rfb=0.38.

EXAMPLE 19

2',4'-di-O-acetyl-23-acetylthio-23-demycinosyl-23-deoxydesmycosin dimethylacetal:

2',4'-di-O-acetyl-23-demycinosyl-23-O-tosyldesmycosin dimethylacetal(1.32 g) and potassium thiolacetate (205 mg, 1.2 equimolar) were dissolved in dimethylformamide (8 ml), and stirred at 70° C. for 2 hours. Reaction mixture was poured into cold 7% aqueous ammonia saturated with sodium chloride and the precipitated porridge-like substance was collected, then dissolved in chloroform. Chloroform solution was washed with 7% aqueous ammonia, passed through Whatman 1PS filter paper and concentrated in vacuo. Residue was charged on a column of silica-gel (Merck Art 7734), and eluted with chloroform (500 ml), followed by chloroform-methanol (100:1). Fractions showing Rfb=0.41 were collected and dried up in vacuo to obtain foamy solid 2',4'-di-O-acetyl-23-acetylthio-23-demycinosyl-23-deoxydesmycosin dimethylacetal (910 mg).

EXAMPLE 20

23-benzythio-23-demycinosyl-23-deoxydesmycosin:

Aqueous solution (0.2 ml) of potassium hydroxide (114 mg, 5 equimolar) and benzylbromide (0.241 ml, 5 equimolar) were added to 2',4'-di-O-acetyl-23-acetylthio-23-demycinosyl-23-deoxydesmycosin (300 mg) and polyethyleneglycole (20 mg) dissolved in benzene (10 ml), and stirred at room temperature for 4 hours. Reaction mixture was adjusted to pH 2–3, and further adjusted to pH 8–9 by 7% aqueous ammonia, then extracted with benzene. Benzene layer was passed through Whatman 1PS filter paper and concentrated in vacuo. Residue was purified by preparative silica-gel TLC (Merck, Art 5717, 20×20 cm, 2 plates) using benzene-acetone (5:1). Band showing Rf=0.43 was scratched off and extracted with chloroform-methanol (3:1). Extract was dried up in vacuo to obtain white foamy solid 2',4'-di-O-acetyl-23-benzylthio-23-demycinosyl-23-deoxydesmycosin (63 mg).

The above product dissolved in methanol (5 ml) and stirred at 55° C. for 5 hours and the reaction mixture was dried up in vacuo to obtain white foamy 23-benzylthio-23-demycinosyl-23-deoxydesmycosin (37 mg).

NMR (CDCl$_3$)

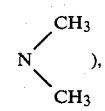

1.77 (s., 3H, C$_{12}$—CH$_3$), 2.52 (s., 6H, 3.69 (s., 2H, —CH$_2$—C$_6$H$_5$), 4.25 (d., 1H, H—1'), 4.78 (d.t., 1H, H—15), 5.65 (d., 1H, H—13), 6.26 (d., 1H, H—10), 7.30 (s., 5H, —C$_6$H$_5$), 7.32 (d., 1H, H—11), 9.69 (s., 1H, CHO)

Mass (EI); 703 (M+), 685 (M+—18), 174, 115
TLC; Rfc=0.36

EXAMPLE 21

2',4'-di-O-acetyl-23-acetylthio-23-demycinosyl-23-deoxydesmycosin diethylacetal:

Trifluoroacetic acid (0.4 ml) was added under heating to 2',4'-di-O-acetyl-23-acethylthio-23-demycinosyl-23-deoxydesmycosin (800 mg) dissolved in ethanol (3.6 ml) and stirred at room temperature for 4.5 hours. Reaction mixture was ice-cooled, adjusted to pH 9 by 7% aqueous ammonia, and extracted with chloroform. Chloroform layer was passed through Whatman 1PS filter paper and concentrated in vacuo to obtain pale yellow foamy solid 2',4'-di-O-acetyl-23-acetylthio-23-demycinosyl-23-deoxydesmycosin diethylacetal (760 mg). TLC: Rfb=0.47

EXAMPLE 22

23-(2-phenylethyl)thio-23-demycinosyl-23-deoxydesmycosin:

Diethylacetal compound obtained in example 21, anhydrous potassium carbonate (500 mg, 7.2 equimolar) and 18-crown-6 (20 mg, 0.15 equimolar) were dissolved in dry acetone (15 ml) and refluxed for one hour. 2-phenylethylbromide (925 μl, 10 euimolar) was added thereto and refluxed for 41 hours. Reaction mixture was cooled, filtered and the filtrate was concentrated in vacuo to obtain oily substance (1.51 g), which was charged on a column of silica-gel (Merck, Art 7734) and eluted with hexane-acetone (12:1). Fractions showing Rfb=0.5 were collected and dried up in vacuo. The eluate was charged on a column (3×9 cm) of silica-gel (Merck, Art 9385), and subjected to flush chromatography eluting with benzene-acetone (15:1). Fractions showing Rfb=0.5 were collected and dried up in vacuo to obtain 2′,4′-di-O-acetyl-23-(2-phenylethyl)thio-23-demycinosyl-23-deoxydesmycosin diethylacetal (23 mg). The product was dissolved in methanol (3 ml) and stirred at 55° C. for 15 hours. Reaction mixture was concentrated in vacuo and 90% trifluoroacetic acid was added to the residue, then stirred for 30 minutes under ice-cooling. 7% aqueous ammonia was added to the reaction mixture to adjust at pH 9, then extracted with chloroform. Extract was washed with water, passed through Whatman 1PS filter paper and concentrated in vacuo to obtain white foamy solid 23-(2-phenylethyl)thio-23-demycinosyl-23-deoxydesmycosin (18 mg).

NMR (CDCl$_3$)

$\delta^{TMS}_{ppm}$;

1.79 (s., 3H, C$_{12}$—CH$_3$), 2.54 (s., 6H,

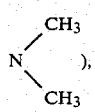), 4.26 (d., 1H, H—1′), 4.79 (m., 1H, H—15), 5.73 (d., 1H, H—13), 6.21 (d., 1H, H—10) 7.21 (s., 5H, —C$_6$H$_5$), 7.30 (d., 1H, H—11), 9.66 (s., 1H, CHO)

Mass (CI); 718 (MH+), 700 (MH+—18), 192, 174, 106

TLC; Rfc=0.36

EXAMPLE 23

23-(1-phenylethyl)thio-23-demycinosyl-23-deoxydesmycosin:

1-phenylethyl bromide (463 μl, 10 equimolar) was added to diacetal compound (203.5 mg) obtained in example 21, potassium carbonate (250 mg) and 18-crown-6 (100 mg, 0.15 equimolar), dissolved in dry acetone (7.5 ml) and refluxed for 17 hours. Reaction mixture was cooled and filtered the insolubles. The filtrate was concentrated in vacuo to obtain yellow oily substance (920 mg), which was charged on a column (3×9 cm) of silica-gel (Merck, Art 9385) and subjected to flush chromatography eluted with benzene-acetone (15:1). Fractions showing Rfb-0.5 were collected and dried up in vacuo to obtain 2′,4′-di-O-acetyl-23-(1-phenylethyl)thio-23-demycinosyl-23-deoxydesmycosin diethylacetal (114 mg).

The product was dissolved in methanol (5 ml) and stirred at 55° C. for 19 hours and the reaction mixture was concentrated in vacuo. 90% aqueous trifluoroacetic acid (1 ml) was added to the residue and stirred for 30 minutes under ice-cooling. 7% aqueous ammonia was added to the reaction mixture to adjust pH 9, then extracted with chloroform. Extract was washed with water, passed through Whatman 1PS filter paper, and concentrated in vacuo to obtain pale yellow foamy solid 23-(1-phenylethyl)thio-23-demycinosyl-23-deoxydesmycosin (74 mg).

NMR (CDCl$_3$)

$\delta^{TMS}_{ppm}$;

1.53 (s., 3H,

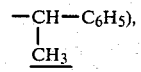

1.79 (s., 3H, C$_{12}$—CH$_3$), 2.50 (s., 6H,

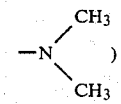

4.25 (d., 1H, H—15), 4.6~5.0 (m., 1H,

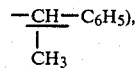

H—13), 6.24 (d., 1H, H—10), 7.30 (d., 1H, H—11), 7.31 (s., 5H, —C$_6$H$_5$), 9.69 (s., 1H, CHO)

Mass (CI); 718 (MH+), 700 (MH+—18), 192, 174, 105

TLC; Rfc=0.35

EXAMPLE 24

23-phenylthio-23-demycinosyl-23-deoxydesmycosin:

KF-Al$_2$O$_3$ (1.5 g) was added to dimethylacetal compound (912 mg 1 mM) obtained in example 4 and thiophenol (510 μl, 5 equimolar) dissolved in acetonitrile (10 ml), and stirred at room temperature for 3 hours. Reaction mixture was filtered and the insolubles are washed with diethyl ether. Combined filtrate and washings are concentrated in vacuo to obtain yellow oil substance (1.19 g), which was charged on a column of silica-gel (20 g, Merck Art 7734) and eluted with benzene-acetone (10:1). Fractions without containing thiophenol were collected and dried up in vacuo to obtain crude substance (516 mg), which was charged on a column of silica-gel (25 g, Merck Art 9385) and eluted with benzene-acetone (10:1) by flush chromatography. Fractions showing Rfb=0.45 were collected and dried up in vacuo to obtain 2′,4′-di-O-acetyl-23-phenylthio-23-demycinosyl-23-deoxydesmycosin dimethylacetal (159 mg).

The above compound dissolved in methanol (5 ml), stirred at 55° C. for 6.5 hours and the reaction mixture was concentrated in vacuo. 90% trifluoroacetic acid (3 ml) was added to the residue and stirred for 30 minutes under ice-cooling. Reaction mixture was adjusted to pH 9 by diluted aqueous ammonia under cooling, and extracted with chloroform. Extract was washed with water, passed through Whatman 1PS filter paper and dried up in vacuo to obtain white foamy solid 23-phenylthio-23-demycinosyl-23-deoxydesmycosin (112 mg).

NMR (CDCl$_3$, FX 100)

$\delta^{TMS}_{ppm}$:

1.68(s., 3H, C$_{12}$—CH$_3$), 2.50(s., 6H, $-N\begin{pmatrix} CH_3 \\ CH_3 \end{pmatrix}$), 4.25(d., 1H, H—1'), 4.89(d.t., 1H, H—15), 5.72(d., 1H, H—13), 6.26(d., 1H, H—10), 7.27(s., 5H, —C$_6$H$_5$), 7.30(d., 1H, H—11), 9.70(s., 1H, CHO)

Mass (CI): 690(MH+), 672(MH+—18), 192, 174.

TLC: Rfc=0.36.

We claim:

1. A compound of the formula or a non-toxic salt thereof, wherein A is oxygen or sulfur; R$_1$ is in which R$_{12}$, R$_{13}$ and R$_{14}$ are each independently selected from the group consisting of hydrogen, lower alkyl, lower alkoxy, halogen, nitro and di-lower alkylamino, or R$_1$ is $$-\underset{R_5}{\overset{R_4}{\underset{|}{\overset{|}{C}}}}-R_3,$$

in which R$_3$ is phenyl and R$_4$ and R$_5$ are each independently selected from the group consisting of hydrogen, lower alkyl and phenyl; and R$_2$ is hydrogen or hydroxyl.

2. A compound according to claim 1, wherein A is oxygen and R$_2$ is hydroxyl.

3. A compound according to claim 2, which is selected from the group consisting of
23-O-benzyl-23-demycinosyldesmycosin,
23-O-triphenylmethyl-23-demycinosyldesmycosin,
23-O-phenyl-23-demycinosyldesmycosin,
23-O-(p-tolyl)-23-demycinosyldesmycosin,
23-O-(p-ethylphenyl)-23-demycinosyldesmycosin,
23-O-(3,5-xylyl)-23-demycinosyldesmycosin,
23-O-(p-methoxyphenyl)-23-demycinosyldesmycosin,
23-O-(p-chlorophenyl)-23-demycinosyldesmycosin,
23-O-(2,4-dichlorophenyl)-23-demycinosyldesmycosin,
23-O-(p-bromophenyl)-23-demycinosyldesmycosin,
23-O-(p-nitrophenyl)-23-demycinosyldesmycosin,
23-O-(m-nitrophenyl)-23-demycinosyldesmycosin,
23-O-(m-diethylaminophenyl)-23-demycinosyldesmycosin, and
23-O-(2,6-di-t-butyl-4-tolyl)-23-demycinosyldesmycosin.

4. A compound according to claim 1, wherein A is sulfur, R$_1$ is phenyl or $$-\underset{R_5}{\overset{R_4}{\underset{|}{\overset{|}{C}}}}-R_3,$$

in which R$_3$ is phenyl and R$_4$ and R$_5$ are each independently selected from the group consisting of hydrogen, lower alkyl and phenyl, and R$_2$ is hydroxyl.

5. A compound according to claim 4, which is selected from the group consisting of
23-phenylthio-23-demycinosyl-23-deoxydesmycosin,
23-benzylthio-23-demycinosyl-23-deoxydesmycosin,
23-(1-phenylethyl)thio-23-demycinosyl-23-deoxydesmycosin, and
23-(2-phenylethyl)thio-23-demycinosyl-23-deoxydesmycosin.

* * * * *